(12) United States Patent
Rutherford et al.

(10) Patent No.: US 11,285,402 B2
(45) Date of Patent: Mar. 29, 2022

(54) DIAMOND PRESSURE APPARATUS FOR CRYSTALLIZING CANNABINOIDS

(71) Applicants: Josh Rutherford, Arvada, CO (US); Spencer Uniss, Boulder, CO (US); Adam Weiss, Boulder, CO (US); Stephen Tolpa, Rockaway, NJ (US)

(72) Inventors: Josh Rutherford, Arvada, CO (US); Spencer Uniss, Boulder, CO (US); Adam Weiss, Boulder, CO (US); Stephen Tolpa, Rockaway, NJ (US)

( * ) Notice: Subject to any disclaimer, the term of this patent is extended or adjusted under 35 U.S.C. 154(b) by 24 days.

(21) Appl. No.: 16/938,911

(22) Filed: Jul. 24, 2020

(65) Prior Publication Data

US 2021/0170301 A1 Jun. 10, 2021

Related U.S. Application Data

(60) Provisional application No. 62/856,657, filed on Jun. 3, 2019.

(51) Int. Cl.
*B01D 9/00* (2006.01)
*C07C 37/68* (2006.01)

(52) U.S. Cl.
CPC ........... *B01D 9/005* (2013.01); *B01D 9/0059* (2013.01); *B01D 9/0063* (2013.01); *C07C 37/68* (2013.01); *B01D 2009/0086* (2013.01); *C07B 2200/13* (2013.01)

(58) Field of Classification Search
CPC ...... B01D 9/005; B01D 9/0059; C07C 37/68; C07B 2200/13
See application file for complete search history.

(56) References Cited

U.S. PATENT DOCUMENTS 7,700,368 B2 * 4/2010 Flockhart ............. C07D 311/80
436/177
10,195,159 B2 * 2/2019 Whittle ................ B01D 11/028

* cited by examiner

*Primary Examiner* — Sikarl A Witherspoon
(74) *Attorney, Agent, or Firm* — Block 45 Legal, LLC

(57) ABSTRACT

An apparatus for purifying diamond CBD oil crystals. A cylindrical glass or metal vessel is provided and supported by least one support post, the vessel having an upper portion and a lower surface having laser etched nucleation sites for initiating crystal growth. A removable head is engageable with the upper portion of the vessel, the head having an uppermost portion and a plurality of ports extending therethrough. A pressurized nitrogen tank is operatively connected to a port of the head, as is a pressure gauge. A safety valve is disposed at the uppermost portion of the head. Optionally, an inline desiccant chamber is also operatively connected to the head. The apparatus crystalizes cannabinoids in either a solventless process or a solvent process.

12 Claims, 1 Drawing Sheet

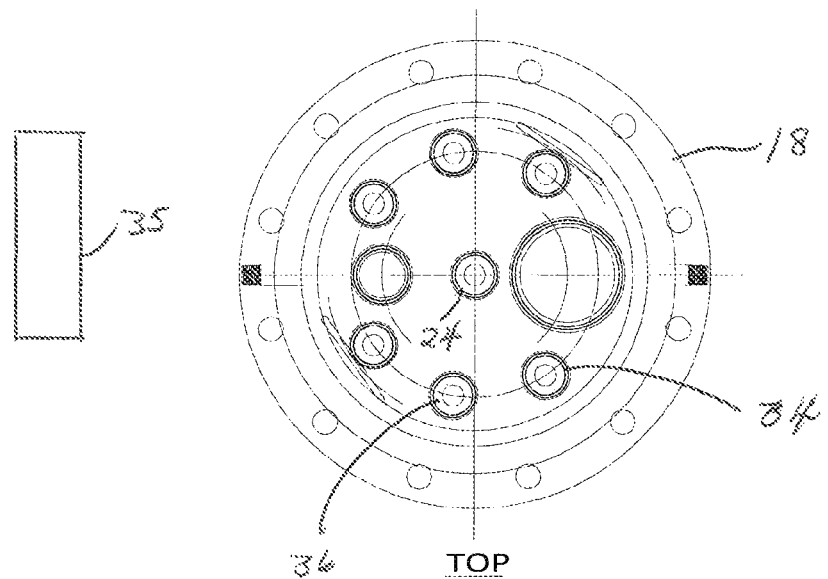
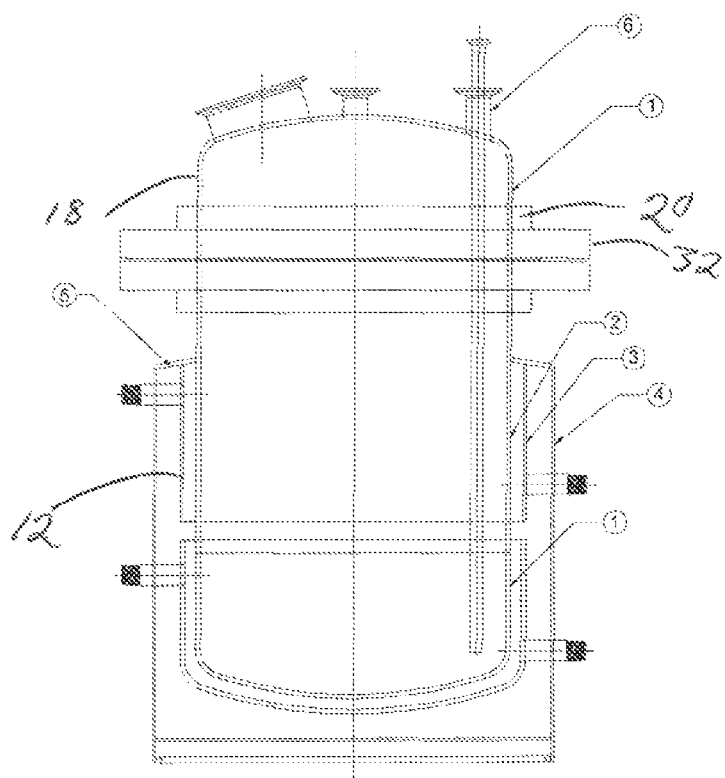

DIAMOND PRESSURE APPARATUS FOR CRYSTALLIZING CANNABINOIDS

RELATED APPLICATION

This patent application is related to copending U.S. provisional patent application No. 62/856,657 for DIAMOND PRESSURE VESSEL FOR CRYSTALIZING CANNABINOIDS, filed Jul. 24, 2019, and hereby incorporates the subject matter thereof by reference.

FIELD OF THE INVENTION

This invention relates to an apparatus for creating high cannabinoid full spectrum extract (HCFSE), high terpene full spectrum extract (HTFSE), live resin, solventless, solvent, and other cannabinoid crystallization, and, more particularly, to an apparatus for creating such crystals with the use of different pressures and pressurized nitrogen in a glass or metal vessel.

BACKGROUND OF THE INVENTION

*Cannabis*, more commonly known as marijuana, is a genus of flowering plants that includes at least three species: *Cannabis sativa*, *Cannabis indicia*, and *Cannabis ruderalis* as determined by plant phenotypes and secondary metabolite profiles.

The use of *cannabis* for social and medical purposes has been known for almost of all humanity's recorded history. *Cannabis* is most commonly administered via inhalation or consumption of marijuana-infused food and drink. However, since 1972 marijuana has been classified as a Schedule I dmg under the U.S. Controlled Substances Act because the U.S. federal government considers it to have "no accepted medical use." In stark contrast to this position, a number of U.S. states and the District of Columbia have recognized the medical benefits of *cannabis* and have decriminalized its medical use.

In 2014, the U.S. Attorney General Eric Holder announced that the federal government would allow states to create a regime that would regulate and implement the legalization of *cannabis*, including loosening banking restrictions for *cannabis* dispensaries and growers.

The U.S. government set a precedent for patenting *cannabis*, and *cannabis*-related inventions. For example, U.S. Pat. No. 6,630,507 issued on Oct. 7, 2003 and assigned on the patent face to The United States of America, is directed to methods of treating diseases caused by oxidative stress by administering therapeutically effective amounts of a cannabidiol (CBD) cannabinoid from *cannabis* that has substantially no binding to the N-methyl-D-aspartate (NMDA) receptor, wherein the CBD acts as an antioxidant and neuroprotectant. A search of the USPTO Patent Application Information Retrieval (PAIR) system reveals the existence of thousands of *cannabis*-related applications and issued patents.

Despite the official position of the U.S. federal government, and as recognized by the states that have legalized it, *cannabis* has been shown to provide substantial benefits for medical and recreational uses. *Cannabis* is regularly used by a wide cross-section of society to treat a variety of maladies, conditions and symptoms including, but not limited to: nausea, glaucoma, lack of appetite, mucous membrane inflammation, epilepsy, leprosy, fever, obesity, asthma, urinary tract infections, coughing, anorexia associated with weight loss in AIDS patients, pain, and multiple sclerosis.

Cannabinoids are terpenophenolic compounds found in *Cannabis sativa*, an annual plant belonging to the cannabaceae family. The plant contains more than 400 chemicals and approximately 70 cannabinoids. The latter accumulate mainly in the glandular trichomes. The most active of the naturally occurring cannabinoids is tetrahydrocannabinol (THC), which is used for treating a wide range of the aforementioned medical conditions.

Cannabidiol (CBD), an isomer of THC, is a potent antioxidant and anti-inflammatory compound known to provide protection against acute and chronic neuro-degeneration; cannabigerol (CBG), found in high concentrations in hemp, which acts as a high affinity; and cannabichromene (CBC), which possesses anti-inflammatory, anti-fungal and anti-viral properties. The term diamond CBD is used by Hempco Food and Fiber Inc. of Burnaby, British Columbia, Canada and others to refer to hemp extracts containing greater than 99% cannabidiol.

Many phytocannabinoids have therapeutic potential in a variety of diseases and may play a relevant role in plant defense as well as in pharmacology. Accordingly, biotechnological production of cannabinoids and cannabinoid-like compounds with therapeutic properties is of utmost importance. Thus, cannabinoids are considered to be promising agents for their beneficial effects in the treatment of various diseases.

One method of cannabinoid preservation includes separating a cannabinoid ethanol (EtOH) mixture from a *cannabis* extract through a filtration process, forming a slurry by combining a crystalline compound with the cannabinoid EtOH mixture, and heating and agitating the slurry in a pressurized chamber to form a colloidal cannabinoid EtOH mixture The colloidal cannabinoid EtOH mixture is distributed into a tray to form an evenly distributed mixture layer. An evaporation vessel is formed for the evenly distributed mixture layer through the attachment of a detachable cover to the tray, and the evaporation vessel is positioned and heated within a heating chamber. A rapid cooling process is performed as the evenly distributed mixture layer approaches saturation temperature, and this process is repeated until crystal formation is detected within the evenly distributed mixture layer. The evaporation vessel is removed from the heating chamber upon detection of crystal formation.

Recrystallizations of cannabinoids from solvents, in particular from non-polar hydrocarbon solvents, are well known in the art. These processes represent a classic recrystallization, where the solvent is heated to increase solubility of the compound to be recrystallized and then cooled, creating a supersaturated solution that grows crystals. Ball jars have been used, but they cannot be pressurized from outside, so internal pressure is created while the contents of the jars are heated to 75° F. to 85° F. This is a time-consuming process often requiring more than a month to create crystals.

Other recrystallization processes include using a second, weak solvent that, when added to the saturated solvent, causes precipitation of crystals. Still other, less common recrystallization techniques exist for specialized crystal growth, such as those made for protein crystallography where a reactant is added to the solvent, producing a compound as it crystallizes.

In all cases, crystal growth is limited by the ability of the molecule to move into regularly ordered, crystalline structures while excluding impurities, without re-dissolving the growing crystals. If heat is applied, the solubility of the compound increases in the solvent and crystallization is limited. Kinetic energy as vibration can be applied, short of heating the solution, to provide kinetic energy for mass transfer without heat. Electrical potentials have been applied to crystal growth, enhancing the process under controlled conditions.

These processes rely on successive recrystallization passes that break down or destroy the previous crystal, release included impurities, and grow a new crystal that is more pure due to dilution of impurities in the solvent during the destruction phase. Crystal manufacturing processes prefer growing by deposition of new material, not purification by rearrangement because their process involves growth, destruction and regrowth. Time for growth has been the limiting factor in performing the recrystallization methods.

DESCRIPTION OF RELATED ART

U.S. Pat. No. 7,700,368 issued to Flockhart, et al., on Apr. 20, 2010 for METHODS OF PURIFYING CANNABINOIDS FROM PLANT MATERIAL discloses methods of preparing cannabinoids in substantially pure form starting from plant material. Also described are substantially pure preparations of various cannabinoids and cannabinoid acids, and also extracts enriched in cannabinoids and cannabinoid acids.

SUMMARY OF THE INVENTION

While recrystallization from a super-saturated solution is well understood, the present invention allows crystal rearrangement and purification to take place in an accelerated time frame by the use of controlled pressure and temperature supplied to the vessel. In addition to accelerated crystal growth, controlling and varying heating and cooling can result in different formation types of crystals. The inventive system can run one or more multi-batch columns depending on the needs and end goal for product formulation. Stacking batches saves money on testing.

Both high cannabinoid full spectrum extract (HCFSE) and high terpene full spectrum extract (HTFSE) are produced by the inventive apparatus from dried bud material, wet/fresh, frozen, or fresh frozen starting material (biomass). Water content is removed from live resin in the vessel with the use of a desiccant chamber operatively connected to the vessel that removes water while the system is under more than 15 psi pressure provided by a pressurized nitrogen tank.

The vessel itself may have laser etched nucleation sites on the bottom or side surface thereof, made of metallic material. Site glasses and dishes, however, are made of glass material. The vessel is six inches or larger and is ASME certified. A safety valve is positioned between the vessel and the pressurized nitrogen tank to prevent over-pressurization. Gauges are provided to indicate the system is sealed. An extraction hose connects to the extraction vessel for the filling thereof, thus allowing for the system to be closed loop. The inventive system preferably resides in a C1D1 area, complying with state and federal laws.

In accordance with the present invention, there is provided an apparatus for purifying diamond CBD oil crystals in a glass or metal container. A removable head is connected to an upper portion of the vessel. A pressurized nitrogen tank is operatively connected to the head, as is a pressure gauge and, optionally, an inline desiccant chamber. A safety valve is also disposed at the uppermost portion of the head.

It is therefore an object of the invention to provide a vessel for purifying diamond CBD oil crystals in a solventless or solvent process.

It is a further object of the present invention to provide a vessel for purifying crystals that uses controlled pressure and temperature supplied to the vessel. Gas (e.g., butane) need not be purged off finally from the vessel, although preferred practice is to do so in vacuum ovens.

It is a further object of the present invention to provide a vessel for purifying crystals, leaving purified crystals in a glass or metal vessel.

It is another object of the present invention to provide a vessel for purifying crystals and removing moisture while the contents of the vessel are under pressure.

These and other objects and advantages of the present invention are more readily apparent with reference to the following detailed description and the accompanying drawings.

BRIEF DESCRIPTION OF THE DRAWINGS

A complete understanding of the present invention may be obtained by reference to the accompanying drawings, when considered in conjunction with the subsequent detailed description, in which:

FIG. 1 is an exploded, schematic view of the diamond pressure apparatus in accordance with the present invention.

DETAILED DESCRIPTION OF THE PREFERRED EMBODIMENT

Although the following detailed description contains specific details for the purposes of illustration, those of ordinary skill in the art will appreciate that variations and alterations to the following details are within the scope of the invention. Accordingly, the exemplary embodiments of the invention described below are set forth without any loss of generality to, and without imposing limitations upon, the claimed invention.

A metal container is provided, specifically a stainless steel vessel in the preferred embodiment, which has a fully opaque sight glass with blinders for observing the process and formation of the purified crystals, a pressure meter, a clamped lid, and means for adjusting the pressure therein. Gas (e.g., butane) need not be purged off finally from the vessel, although preferred practice is to do so in vacuum ovens.

Referring now to FIG. 1, in the preferred embodiment, there is shown a vessel 12 with a surrounding insulating jacket. On one end of a quick-disconnect coupler 24 connected to a removable head 18 is an inline desiccant chamber 32. Desiccant chamber 32 has a ball valve so an operator can expose the atmosphere in vessel 12 to the desiccant for as long as necessary to remove the desired amount of water. The desiccant itself is a self-indicated silica gel, held in place by Viton screen gasket 20. Desiccant chamber 32 need not be included in alternate embodiments of the inventive apparatus. The inventive apparatus can run one or more multi-batch columns depending on the needs and end goal for product formulation. Stacking batches saves money on testing.

At the uppermost portion of head 18 is a safety valve 34 set to prevent over-pressurization of vessel 12. Gas (e.g., butane) need not be purged off finally from the vessel, although preferred practice is to do so in vacuum ovens.

Removable head 18 has a plurality of ports to which can be attached, respectively, inline desiccant chamber 32, safety valve 34, a pressurized nitrogen tank 35, and a pressure gauge 36. It should be understood that the ports on head 18 can be reconfigured depending on a user's requirements. That is, any port can be used to receive nitrogen or communicate with a pressure gauge or act as a pressure valve or facilitate an inline desiccant chamber. The version of ports shown in FIG. 1 is merely one of numerous possible configurations and is not intended to limit conceivable configurations.

Pressure and temperature are supplied to vessel 12 in jacketed vessel for 2-4 weeks. During this time, THC acid crystals precipitate out and fall to the bottom of the vessel 12.

Pressure ranges for different sizes and shapes of diamond type formations can be adjusted. In the preferred embodiment, the pressure range is approximately 10 psi-120 psi. By increasing the pressure, larger sized diamonds are formed, with a much faster turnaround.

Similarly, in the preferred embodiment, temperature ranges are from approximately 0 degrees to 125 degrees Fahrenheit. When using colder temperatures in conjunction with the aforementioned pressure ranges, a higher quality, more translucent diamond is formed, but the turnaround time on this process does takes longer and additional purging of a solvent is required.

In summary, when using hotter temperatures in conjunction with the aforementioned pressure ranges results in a faster turnaround time in the purging process and the formation process.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a great number of variations of the devices, device components, and method steps set forth in the present description. As will be obvious to one of skill in the art, methods and devices useful for the present methods can include a great number of optional composition and processing elements and steps.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in any composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of," and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Since other modifications and changes varied to fit particular operating requirements and environments will be apparent to those skilled in the art, the invention is not considered limited to the example chosen for purposes of disclosure and covers all changes and modifications which do not constitute departures from the true spirit and scope of this invention.

Having thus described the invention, what is desired to be protected by Letters Patent is presented in the subsequently appended claims.

What is claimed is:

1. An apparatus for purifying diamond CBD oil crystals, comprising:
   a) a cylindrical glass vessel supported by least one support post, the vessel having an upper portion and a lower surface having laser etched nucleation sites for initiating crystal growth;

b) a removable head engageable with the upper portion of the vessel, the head having an uppermost portion and a plurality of ports extending therethrough;

c) a pressurized nitrogen tank operatively connected to a port of the head;

d) a pressure gauge operatively connected to a port of the head; and e) a safety valve disposed at the uppermost portion of the head.

2. The apparatus for purifying diamond CBD oil crystals in accordance with claim 1, further comprising an inline desiccant chamber operatively connected to the head.

3. The apparatus for purifying diamond CBD oil crystals in accordance with claim 1, wherein the apparatus crystalizes cannabinoids in a solventless process.

4. The apparatus for purifying diamond CBD oil crystals in accordance with claim 1, wherein the apparatus crystalizes cannabinoids in a solvent process.

5. The apparatus for purifying diamond CBD oil crystals in accordance with claim 1, wherein the pressure range is approximately 10 psi-120 psi and the temperature range is from approximately 0 degrees to 125 degrees Fahrenheit.

6. The apparatus for purifying diamond CBD oil crystals in accordance with claim 1, wherein the at least one support post comprises at least one stainless steel post.

7. An apparatus for purifying diamond CBD oil crystals, comprising:

a) a cylindrical metal vessel supported by least one support post, the vessel having an upper portion and a lower surface having laser etched nucleation sites for initiating crystal growth;

b) a removable head engageable with the upper portion of the vessel, the head having an uppermost portion and a plurality of ports extending therethrough;

c) a pressurized nitrogen tank operatively connected to a port of the head;

d) a pressure gauge operatively connected to a port of the head; and e) a safety valve disposed at the uppermost portion of the head.

8. The apparatus for purifying diamond CBD oil crystals in accordance with claim 7, further comprising an inline desiccant chamber operatively connected to the head.

9. The apparatus for purifying diamond CBD oil crystals in accordance with claim 7, wherein the apparatus crystalizes cannabinoids in a solventless process.

10. The apparatus for purifying diamond CBD oil crystals in accordance with claim 7, wherein the apparatus crystalizes cannabinoids in a solvent process.

11. The apparatus for purifying diamond CBD oil crystals in accordance with claim 7, wherein the pressure range is approximately 10 psi-120 psi and the temperature range is from approximately 0 degrees to 125 degrees Fahrenheit.

12. The apparatus for purifying diamond CBD oil crystals in accordance with claim 7, wherein the at least one support post comprises at least one stainless steel post.

\* \* \* \* \*